US011067500B2

(12) United States Patent
Abasahl et al.

(10) Patent No.: US 11,067,500 B2
(45) Date of Patent: Jul. 20, 2021

(54) PILLAR PHOTONIC CRYSTAL

(71) Applicant: Infineon Technologies AG, Neubiberg (DE)

(72) Inventors: Banafsheh Abasahl, Münster (DE); Anisuzzaman Boni, Berlin (DE); Thomas Grille, Villach (AT); Bernhard Jakoby, Linz (AT); Reyhaneh Jannesari, Plesching (AT)

(73) Assignee: INFINEON TECHNOLOGIES AG, Neubiberg (DE)

(*) Notice: Subject to any disclaimer, the term of this patent is extended or adjusted under 35 U.S.C. 154(b) by 0 days.

(21) Appl. No.: 16/817,874

(22) Filed: Mar. 13, 2020

(65) Prior Publication Data
US 2020/0319095 A1  Oct. 8, 2020

(30) Foreign Application Priority Data

Apr. 3, 2019 (EP) .................................... 19167125

(51) Int. Cl.
G01N 21/3504 (2014.01)
G01N 33/00 (2006.01)
G02B 1/00 (2006.01)

(52) U.S. Cl.
CPC ....... G01N 21/3504 (2013.01); G01N 33/004 (2013.01); G02B 1/005 (2013.01)

(58) Field of Classification Search
CPC ............. G01N 21/3504; G01N 33/004; G01N 33/0027; G02B 1/005
See application file for complete search history.

(56) References Cited

U.S. PATENT DOCUMENTS

| 2005/0084195 | A1 | 4/2005 | Hamann et al. |
| 2005/0281524 | A1 | 12/2005 | Mouli |
| 2007/0034978 | A1* | 2/2007 | Pralle ....................... G01J 3/108 257/432 |
| 2009/0002701 | A1 | 1/2009 | Fattal et al. |
| 2011/0019183 | A1* | 1/2011 | Ukon .................. G01N 21/3504 356/51 |
| 2012/0206726 | A1* | 8/2012 | Pervez .................. G01J 3/0205 356/402 |

FOREIGN PATENT DOCUMENTS

WO   2006007446 A2   1/2006

OTHER PUBLICATIONS

Wook-Jae Lee, "Ultracompact bottom-up photonic crystal lasers on silicon-on-insulator" Aug. 2017 (Year: 2017).*
Reyhaneh Jannesari, "Hybrid Photonic Crystal-Surface Plasmon Polariton Waveguiding System for On-Chip Sensing Applications", Nov. 21, 2018 (Year: 2018).*

* cited by examiner

Primary Examiner — Maurice C Smith
(74) Attorney, Agent, or Firm — Slater Matsil, LLP

(57) ABSTRACT

Techniques (e.g., implemented in devices, methods and/or in non-transitory storage units) are used for confining wavelengths, e.g., using a pillar photonic crystal. A semiconductor device includes a pillar photonic crystal including a structure and a plurality of pillars extending from the structure in a height direction, wherein the plurality of pillars form at least one waveguide for electromagnetic radiation at a specific wavelength, the at least one waveguide extending in at least one planar direction, wherein the structure includes a confining layer in doped semiconductor material to support propagation of surface plasmon polaritons.

13 Claims, 7 Drawing Sheets

 
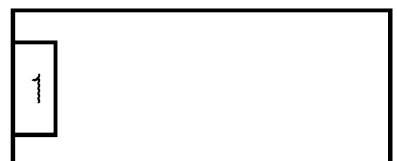 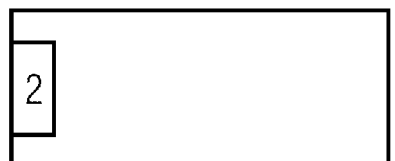
Fig. 3-1  Fig. 3-2
 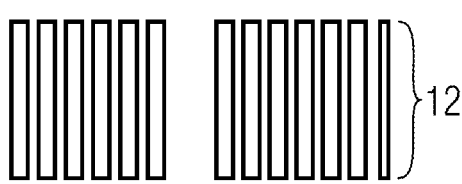
 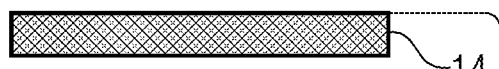
 
Fig. 3-3  Fig. 3-4
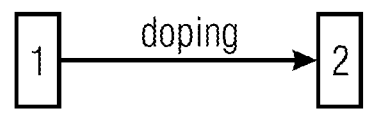
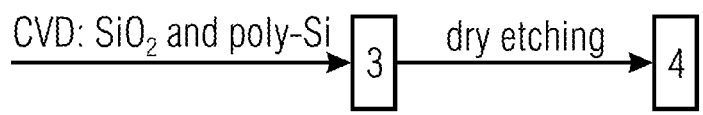
Fig. 3-5

PILLAR PHOTONIC CRYSTAL

This application claims the benefit of European Patent Application No. 19167125.4, filed on Apr. 3, 2019, which application is hereby incorporated herein by reference.

TECHNICAL FIELD

Examples refer to a semiconductor device having a pillar photonic crystal.

Examples also refer to a gas sensor including the semiconductor device.

Examples also refer to a method for spatially confining electromagnetic radiation at a specific wavelength.

Examples also refer to a method for measuring a quantity of specific gas.

Examples also refer to non-transitory storage unit containing instructions which, when executed by a processor, cause the processor to control a method as above and/or below and/or to implement one of the devices above and/or below.

BACKGROUND

A conventional step-index waveguide may be used, for example, for a gas sensor. A conventional step-index waveguide permits an electromagnetic radiation at a particular wavelength to interact with a gas whose amount is to be measured. However, the main portion of the energy is guided inside a main refractive index region, while only the evanescent field of the electromagnetic radiation interacts with the gas to be measured. Therefore, conventional step-index waveguides are inherently inefficient.

However, it has not been easy to find effective alternative techniques which could be actually used in the industry.

Hereinafter, the possibility of using pillar photonic crystals, e.g., for applications such as gas sensing, is briefly discussed.

A pillar photonic crystal affects the motion of photons at a particular wavelength. A pillar photonic crystal comprises an array of pillars displaced periodically along a plane, so that the heights of the pillars extend in a height (vertical) direction perpendicular to the plane. The pillars are disposed so as to form a spatially periodic variation in the refractive index in the intent of forbidding propagation of certain frequencies of electromagnetic radiation (e.g., infra-red, IR, rays and/or visible light) in at least one planar (lateral) direction. Photonic crystals have been obtained which present selected local disruptions, such as missing pillars in the periodic array, hence forming a waveguide, which permits electromagnetic radiation at a specific wavelength to propagate.

A waveguide obtained by a pillar photonic crystal may be used for a gas sensor, for example. If the space between the pillars is replenished with, for example, a mixture of gasses and the structural features of the photonic crystal are associated to a specific wavelength which is the wavelength of maximum absorption of one specific gas of the mixture, properties of the specific gas (e.g., its amount in the mixture) may be determined. Notably, the interaction of the specific wavelength directly interacts with the gas, and not only the evanescent field.

Notwithstanding, it is in general not easy to manufacture a waveguide obtained by a pillar photonic crystal which could be used satisfactorily and with the necessary reliability.

While, with the photonic crystal, it is possible to obtain a lateral containment of the specific wavelength by confining the specific wavelength in one particular planar direction, it is more difficult to obtain a vertical confinement (e.g., in the direction of extension of the pillars).

Accordingly, it would be beneficial to increment the aspect ratio of the pillars (i.e., the ratio between the height and the diameter of the pillars), which is, notwithstanding, challenging for mass production, e.g., by virtue of the intrinsic difficulty in manufacturing such elongated structures.

Therefore, waveguide obtained by pillar photonic crystals may suffer from the difficulty in obtaining vertical confinement, or the difficulty in manufacturing them with the necessary height. At least for these reasons, their actual implementation in the industry is in general not widespread.

Techniques are necessary for permitting an efficient vertical confinement and attaining an easier production of pillar photonic crystals, e.g., to effectively use pillar photonic crystals for applications such as gas sensing.

SUMMARY

In accordance to examples, there is provided a semiconductor device, comprising:

a pillar photonic crystal including a structure and a plurality of pillars extending from the structure in a height direction, wherein the plurality of pillars form at least one waveguide for electromagnetic radiation at a specific wavelength, the at least one waveguide extending in at least one planar direction, wherein the structure includes a confining layer in doped semiconductor material to support propagation of surface plasmon polaritons, SPPs.

It has been understood that, according, a vertical confinement in the height direction may be properly obtained.

Moreover, the height of the pillars in the height direction may be associated to the length of a vertical mode distribution of the electromagnetic radiation at the specific wavelength.

Accordingly, the height of the pillars does not need to be excessive and, therefore, reliability is increased.

In accordance to examples, there is provided an optical gas sensor for measuring the amount of a specific gas, comprising:

the semiconductor device as above and/or below; and an optical detector to detect electromagnetic radiation at the specific wavelength, wherein the specific wavelength is the wavelength of maximum absorption of the specific gas; and the optical detector is configured to measure the intensity of the electromagnetic radiation at the specific wavelength, so that it is possible to determine the amount of the specific gas on the basis of the intensity of the electromagnetic radiation.

Notably, the gas to be measured invested by the radiation directly in the wavelength, hence greatly increasing the efficiency. In particular, not only the evanescent field is used.

In accordance to examples, there is provided a method for spatially confining electromagnetic radiation at a specific wavelength, the method comprising:

confining the electromagnetic radiation in a lateral direction through a pillar array extending in a height direction and forming a photonic crystal; and confining the electromagnetic radiation in a height direction by plasmonic effect, through a confinement layer extending in a planar direction perpendicular to the height direction, the confinement layer being in doped semiconductor material.

In accordance to examples, there is provided a method for measuring a quantity of specific gas, the specific gas being associated to a specific wavelength of maximum absorption, the method comprising:

confining the electromagnetic radiation at the specific wavelength of maximum absorption, as above and/or below, in an environment including the specific gas; and measuring the intensity of the electromagnetic radiation at the specific wavelength of maximum absorption to estimate the amount of the specific gas In accordance to examples, there is provided a method for manufacturing a semiconductor device, comprising:

doping a layer of a semiconductor;

depositing a non-doped layer of semiconductor over the doped layer of semiconductor; and selectively removing material from the non-doped layer of semiconductor so as to obtain an array of pillars so as to obtain a photonic crystal at a specific for a specific wavelength.

In accordance to examples, there is provided a method for manufacturing an optical gas sensor for measuring the amount of a specific gas, the method comprising:

performing a method as above and/or below for manufacturing a semiconductor device with a pillar photonic crystal; and applying an optical detector configured to detect the specific wavelength.

In accordance to examples, there is provided a non-transitory storage unit containing instructions which, when executed by a processor, cause the processor to control a method as above and/or below.

BRIEF DESCRIPTION OF THE DRAWINGS

FIG. 2 shows a field distribution for the device in FIG. 1a;

FIGS. 3-1 to 3-6 show steps for a method for manufacturing a semiconductor device according to examples;

FIG. 4 shows a schematic of a gas sensor according to an example;

DETAILED DESCRIPTION OF ILLUSTRATIVE EMBODIMENTS

Figure 1:
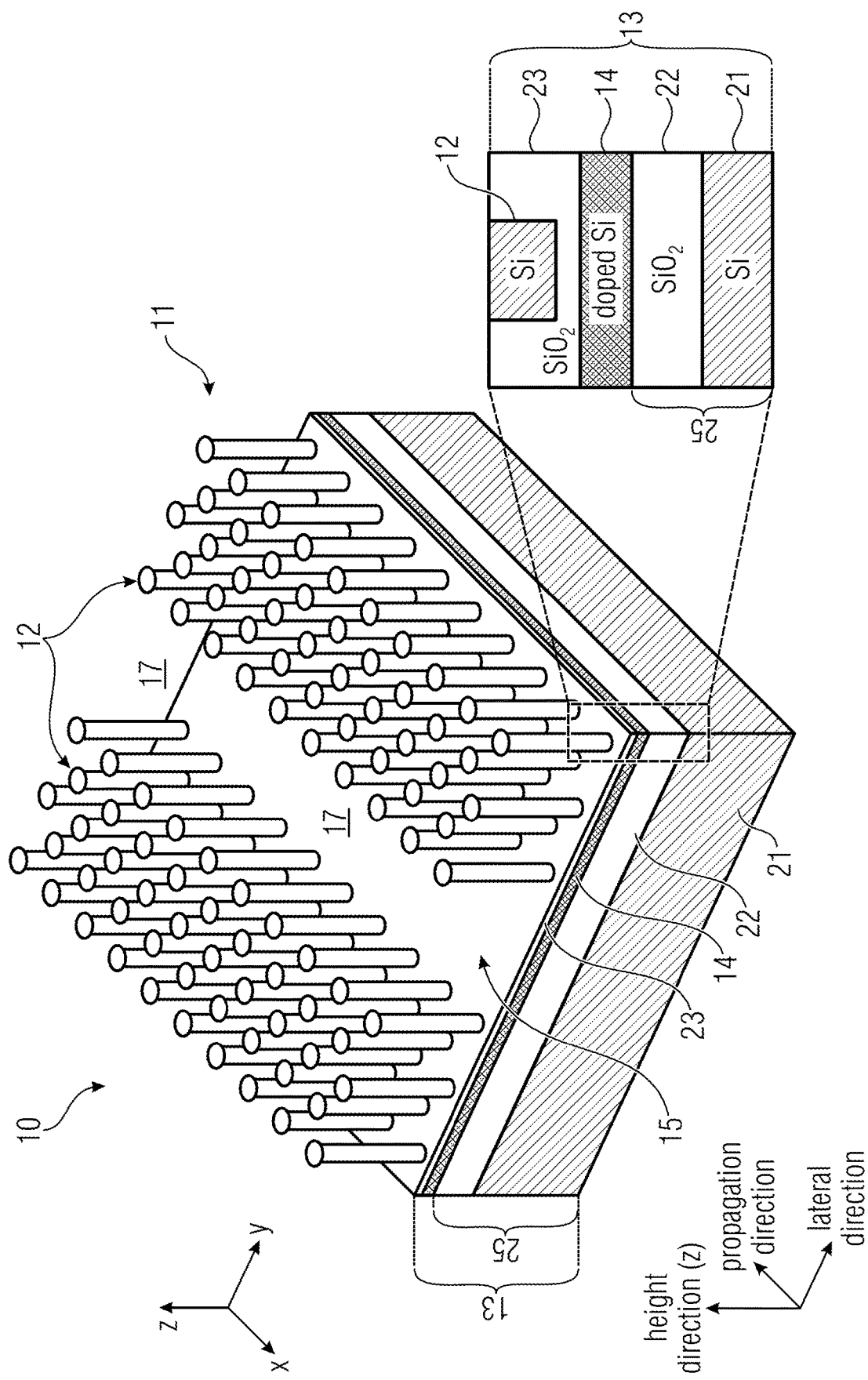
FIGS. 1 and 1a show semiconductor devices according to examples.

FIG. 1 shows a semiconductor device 10. The semiconductor device 10 may be used, for example, for a gas sensor, but other applications may be possible. The semiconductor device (or the gas sensor) may be or be contained in an on-chip device. The semiconductor device (or the gas sensor) may be or be contained in a package-like device.

The semiconductor device 10 may comprise a pillar photonic crystal 11, having a structure 13 and a plurality of pillars (rods) 12 extending from the structure 13. The structure 13 may be mainly developed along a plane (here represented as a horizontal plane), which is here represented as being associated to (e.g., generated by) axes x and y. The horizontal plane x, y may be parallel to the main planes along which the chip or package is developed. The pillars 12 may extend in a height direction (here represented as a vertical direction), which is represented in FIG. 1 by axis z. The axis z may be perpendicular to axes x, y.

The structure 13 may be a layered structure. The layers of the structure 13 may each have a thickness which may be measured in the height (vertical) direction (axis z). In case the semiconductor device 10 is used for a gas sensor, the space 17 free from the structure 13 and the pillars 12 may be replenished by a mixture of gasses in which the amount of a specific gas is to be measured among other gasses.

Structural properties of the pillars 12 (e.g., geometrical properties and/or properties associated to the material, such as the refraction index) may be associated to a specific wavelength of radiation, wherein the radiation at the specific wavelength is to be contained in at least one planar direction (e.g., lateral direction). The distances between consecutive pillars 12 and their diameters may be chosen so as to perform a lateral confinement for one narrow range of radiations (e.g., a wavelength or specific wavelengths), hence prohibiting the propagation of the radiation at a specific wavelength in the lateral direction. The array of pillars may be periodical, e.g., in one or two planar directions, the distance between two consecutive pillars representing the spatial period in one or two planar directions. The array of pillars may be bi-dimensional, forming a matrix of pillars. The pillars 12 are displaced (e.g., as an array) to form a spatially periodic variation in the refractive index in the intent of forbidding propagation of the specific wavelength of the electromagnetic radiation (e.g., infra-red, IR, rays and/or visible light) in at least the lateral direction.

In examples, the material for the pillars 12 may be or comprise silicon (e.g., polysilicon). In examples, the structural properties of the pillars 12 are such that the specific wavelength to be trapped is 4.26 µm, which is the wavelength of maximum absorption of carbon dioxide ($CO_2$). The period in one direction (e.g., in the direction of propagation according to the wavelength) may be, for example, a multiple of the specific wavelength(s) to be trapped (e.g., 4.26 µm). Other wavelengths (e.g., in the mid-IR region or in the visible light region) may be chosen (e.g., for obtaining gas sensors which are sensitive to gasses different from carbon dioxide).

The semiconductor device 10 may comprise a waveguide 15. The waveguide 15 may be formed by the absence of pillars 12, which may be, for example, displaced along a propagation direction. As can be seen from FIG. 1, the propagation direction is a planar direction in the sense that is in the plane x, y, but is not necessarily coincident with any of axes x and y. While radiation is in general allowed to propagate in the propagation direction of the waveguide, only radiation at the specific wavelength is forbidden from propagating in a lateral direction perpendicular to the propagation direction. Both the propagation direction and the lateral direction are planar directions which may be coincident to (or may be linearly dependent from) the axes x and y in FIG. 1. Therefore, radiation at the specific wavelength (as defined by the array of pillars 12) may be trapped laterally but may propagate along the propagation direction defined by the waveguide 15.

It has been noted that, by implementing the structure 13 to include a confining layer 14, a vertical confinement of the radiation at the specific wavelength may be obtained, hence increasing the efficiency of the photonic crystal 11.

In particular, it has been understood that it is possible to confine the radiation at the specific wavelength by exciting surface plasmon polaritons (SPPs).

SPPs are IR or visible-frequency electromagnetic waves propagating along an interface between the structure 13 and the space 17 (which is replenished with gas or a mixture of gas). SPPs involve both charge motion in the highly doped semiconductor material ("surface plasmon") and electromagnetic waves in the space 17 ("polaritons"). The surface plasmon is a surficial oscillation of free electrons in the highly doped semiconductor material of the confining layer 14. SPPs are surface waves, guided along the interface, e.g., in a way similar to that according to which light is guided by an optical fiber. SPPs present tighter spatial confinement and higher local field intensity.

Therefore, while the propagation of the radiation at the specific wavelength in the planar directions (both the propagation direction and the lateral direction) is governed by the effect of the photonic crystal as operated by the array of pillars 12, the vertical propagation is prevented by the SPPs.

The confining layer 14 may be, for example, made of highly doped semiconductor material. The concentration of charges may be in the range between $10^{19}$ cm$_{-3}$ and $10^{21}$ cm$^{-3}$. The charges may be, for example, negative charges. The confining layer 14 may be, for example, a thin film. The confining layer may have a thickness of less than 400 nm, or, more preferably, between 50 nm and 100 nm, e.g., 100 nm or about 100 nm. The preferred material may be silicon.

The complex relative permittivity (e.g., expressed as a ratio relative to the complex permittivity of the vacuum) may be in general expressed with $\varepsilon_r(\omega)=\varepsilon'(\omega)+j\varepsilon''_r(\omega)$, where $\omega$ is the pulse ($2\pi$-times the frequency of the radiation), $\varepsilon'_r(\omega)$ is the real part, and $\varepsilon''_r(\omega)$ is the imaginary part. In particular in the mid-IR region (e.g., around 4.26 μm), the semiconductor material may be chosen so as to have the real part $\varepsilon'_r(\omega)$ to be negative ($\varepsilon'_r(\omega)<0$) and/or to have the imaginary part $\varepsilon''_r(\omega)$ to be a value (e.g., in the range between −1 and 0, e.g. $-1<\varepsilon''(\omega)<0$) which does not cause excessive damping.

By vertically confining the radiation because of the SPPs, it is also possible to define the heights of the pillars 12 so as to be associated to specific wavelength of the radiation to be confined. Accordingly, the height of the pillars 12 in the height direction (axis z) may be the length, or more in general may be associated to the length (e.g., a multiple value) of a vertical mode distribution of the electromagnetic radiation at the specific wavelength. For example, the height of the pillars 12 (from the surface of the structure 13 to the summit of each pillar 12) may be between $6\lambda_o$ and $14\lambda_o$, or preferably, between $8\lambda_o$ and $12\lambda_o$, or more preferably $10\lambda_o$ or around $10\lambda_o$ (where $\lambda_o$ is the particular specific wavelength of the radiation to be confined), without considering the SPP.

By defining the height of the pillars 12 in association to the length of a vertical mode distribution of the electromagnetic radiation at the specific wavelength, the advantage is attained that the height of the pillars 12 may be reduced; otherwise, in an attempt to increase vertical confinement, the height of the pillars 12 would be increased, up to a point of causing difficulties in the production of the pillars 10. Hence, the aspect ratio may be less challenging than in the prior art.

As can be seen from FIG. 1, the layered structure 13 may comprise at least one of the following layers:
a substrate layer 25, which may comprise:
a first substrate sublayer 21, e.g., in silicon;
a second substrate sublayer 22, e.g., in silicon dioxide;
a highly doped confinement layer 14;
a thin non-doped semiconductor layer 23 (e.g., in silicon dioxide).

The pillars 12 may therefore protrude from the thin non-doped semiconductor layer 23 or protrude from the highly doped confinement layer 14.

Figure 1A:
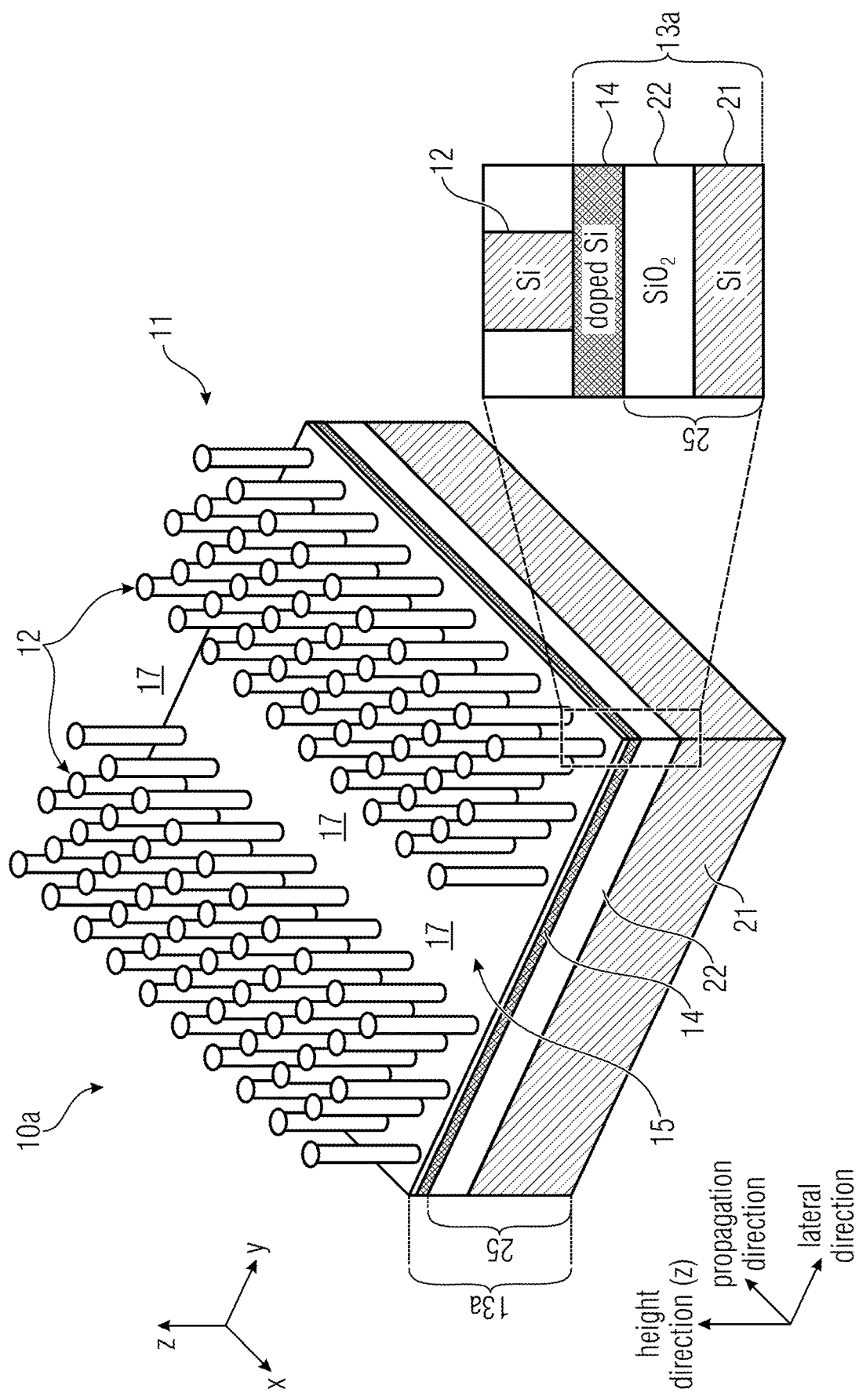

A variant to the device 10 of FIG. 1 is the device 10a of FIG. 1a. Here, the layered structure 13a does not comprise the thin non-doped semiconductor layer 23. The layered structure 13a may comprise at least one of the following layers:
a substrate layer 25, which may comprise:
a first substrate sublayer 21, e.g., in silicon;
a second substrate sublayer 22, e.g., in silicon dioxide;
a highly doped confinement layer 14.

The pillars 12 may therefore protrude from the second substrate sublayer 22 and the highly doped confinement layer 14 siting between them or protrude from the highly doped confinement layer 14.

The remaining features of the device 10a may be like at least some of the features of the device 10 and are therefore not repeated.

Figure 2:
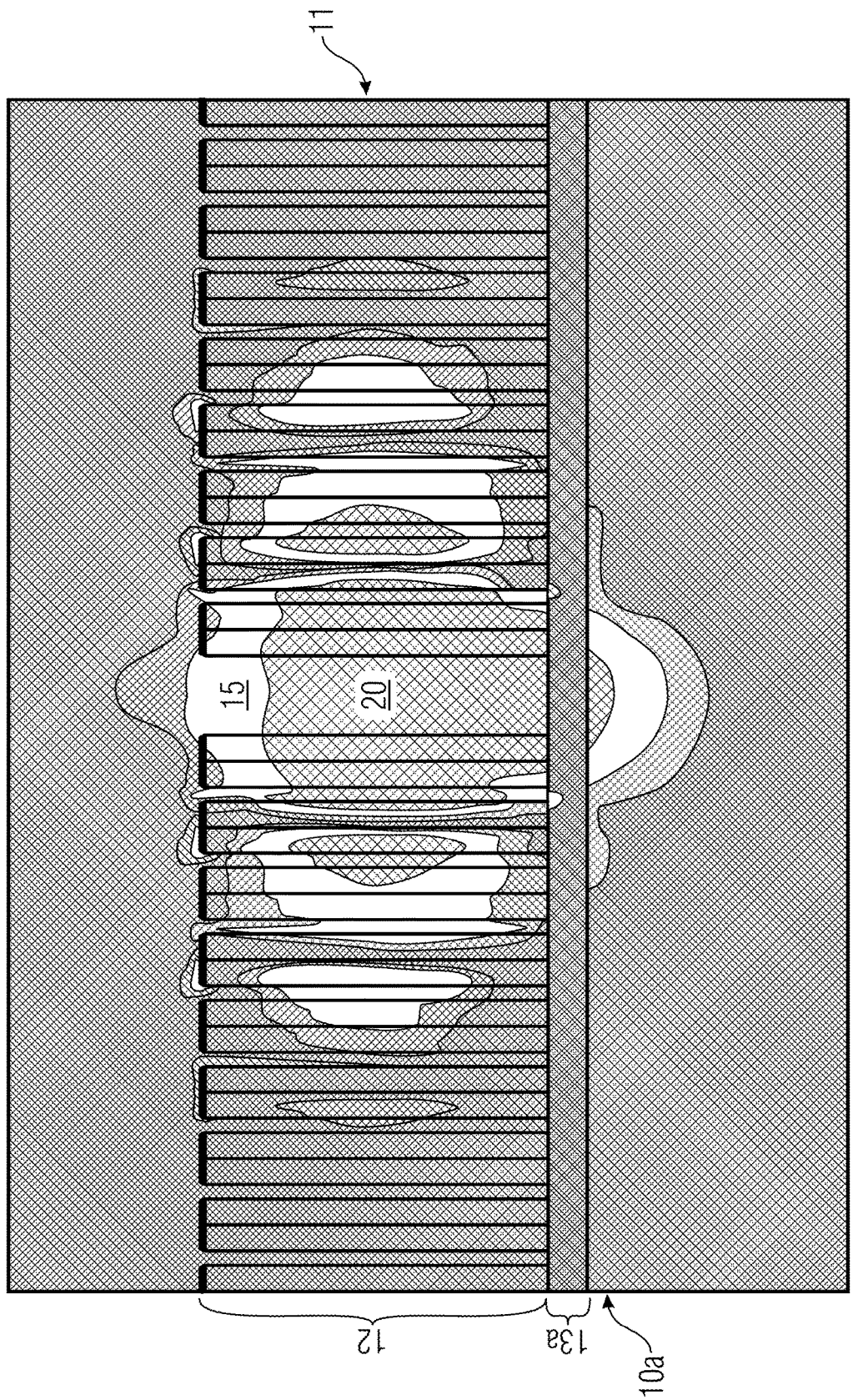
Figure 2A:
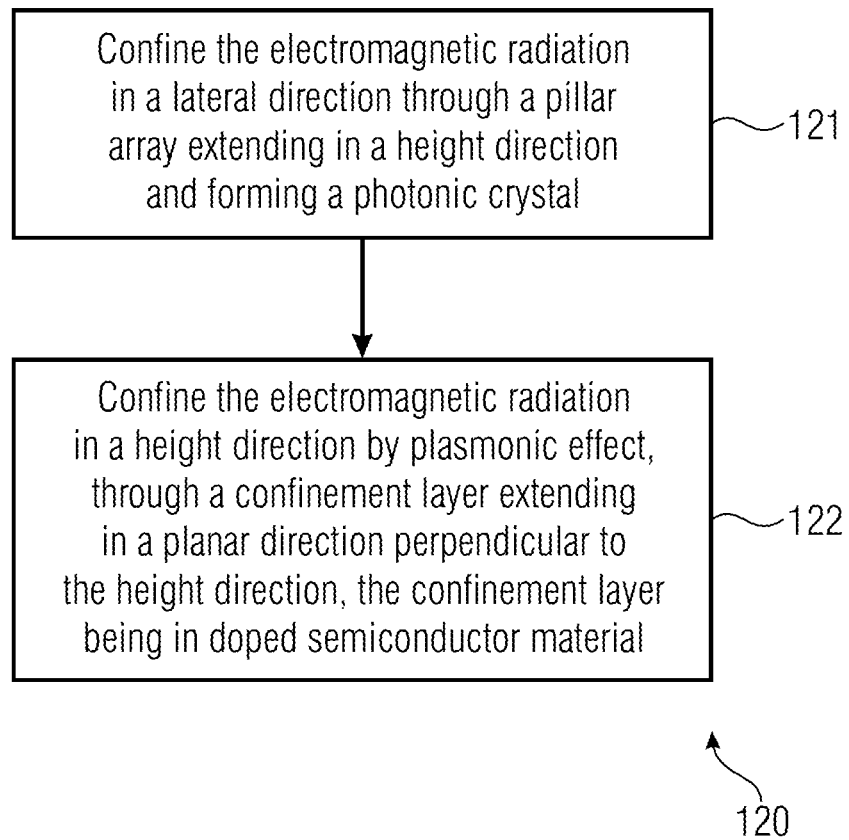
FIG. 2a shows a method for confining radiation according to an example.

A simulation on device 10a of FIG. 1a has been performed. FIG. 2 shows a distribution 20 of the squared field intensity $E^2$ in correspondence to the waveguide 15. The areas which are different from the area 20 correspond to field intensity which may be approximated to zero. The successful vertical confinement may be appreciated.

As shown by FIG. 2, it is possible to perform (e.g., using equipment discussed above and/or below) a method 120 for spatially confining electromagnetic radiation at a specific wavelength, the method comprising:

(step 121) confining the electromagnetic radiation in a lateral direction through a pillar array (e.g., 12) extending in a height direction (e.g., z) so as to form a photonic crystal (e.g., 11); and/or (step 122) confining the electromagnetic radiation in a height direction (e.g., z) by plasmonic effect, through a confinement layer (e.g., 14) extending in a planar direction perpendicular to the height direction (e.g., z), the confinement layer (e.g., 14) being in doped semiconductor material.

The method may permit the electromagnetic radiation at specific wavelength(s) (e.g. 4.26 μm) to propagate according to a propagation direction defined by a waveguide (e.g., 15).

FIGS. 3-1 to 3-6 show steps for manufacturing a semiconductor device such as the device 10 or 10a. In the passages, the device 10 or 10a is shown as vertically exploded to increase intelligibility. FIGS. 3-5 and 3-6 resume the passages.

According to a method, a substrate layer may be made. In particular, a first substrate sublayer 21 and a second substrate sublayer 22 over the first substrate layer 21 may be made.

Figures 3, 4, 5, 6:
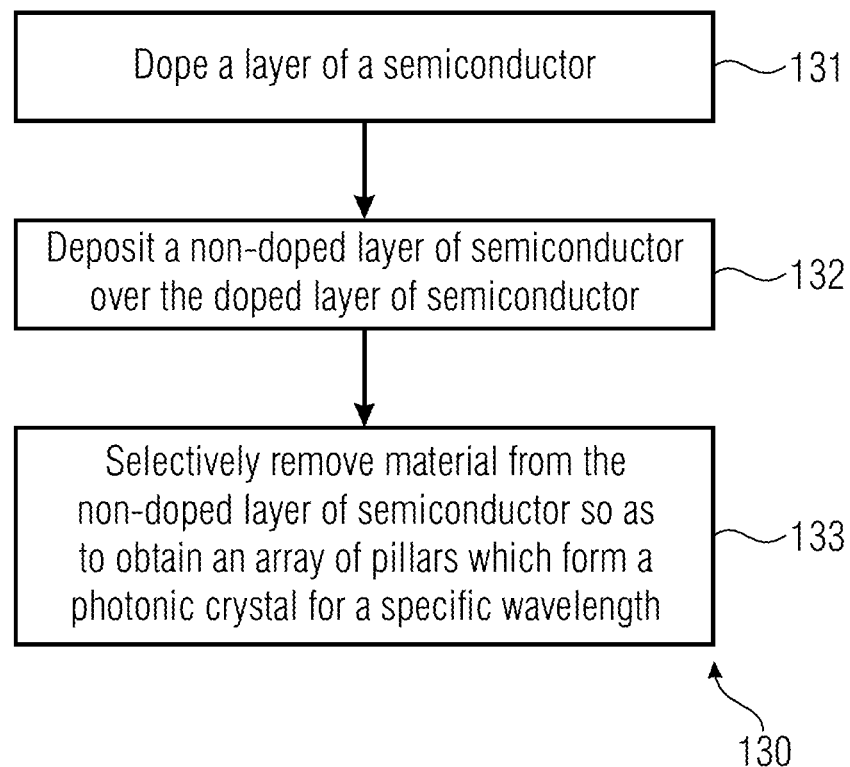
Figure 4:
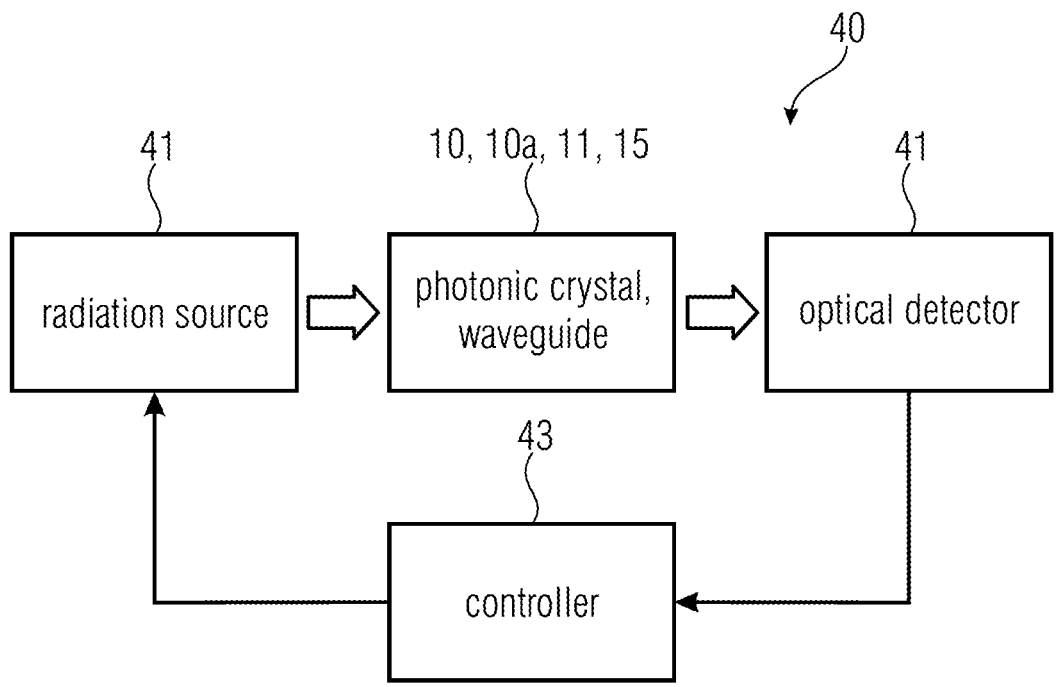
Figure 4A:
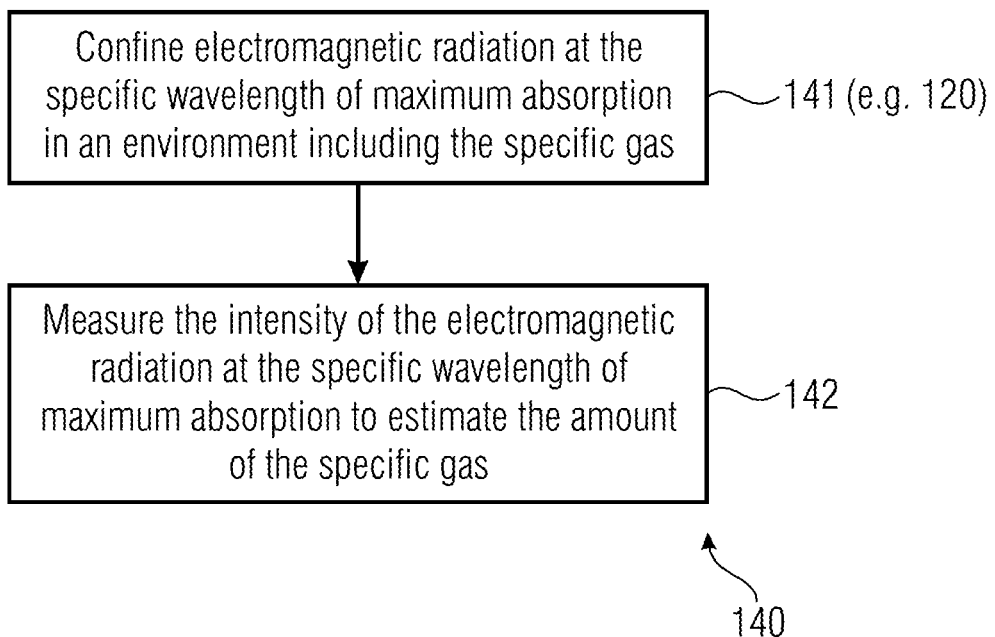
FIG. 4a shows a method for measuring the quantity of a gas according to an example.
Figure 4B:
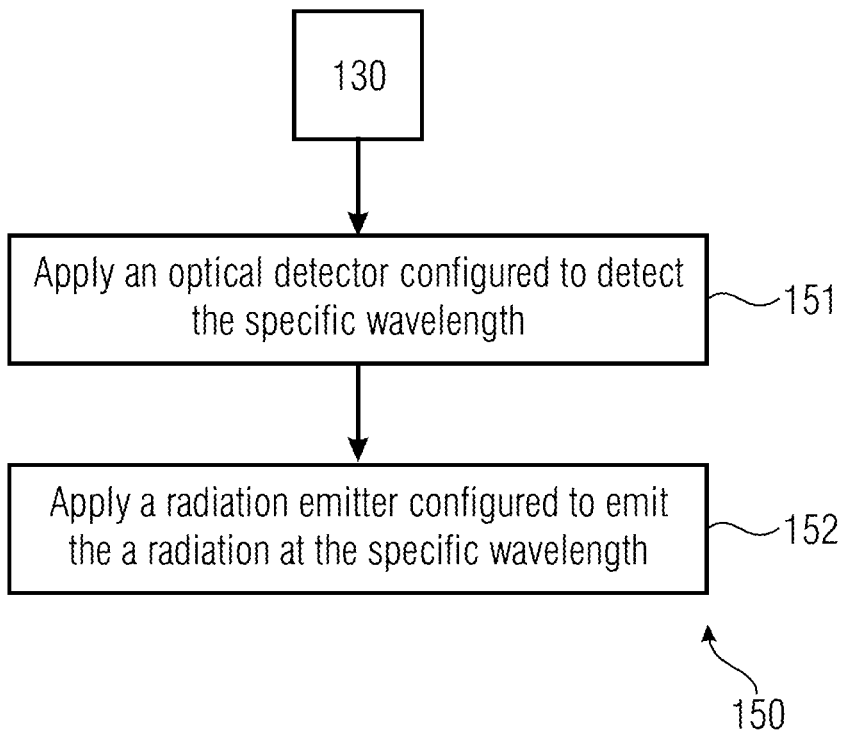
FIG. 4b shows a method for manufacturing a gas sensor of FIG. 4.

FIG. 3-1 shows the substrate layer 25 which may be formed by the first substrate sublayer 21 and the second substrate layer 22.

The first substrate sublayer 21 may be in non-doped semiconductor material (e.g., silicon).

The second substrate layer 22 may be in silicon dioxide (which may be used to prevent the migration of dopants from the highly doped layer 14, to be prepared subsequently).

Over the substrate layer 25 (21, 22), a semiconductor layer 14' in semiconductor material (e.g., silicon) may deposited or otherwise made. The semiconductor layer 14' may be the precursor of the confinement layer 14.

In the transition towards FIG. 3-2, the layer 14' may be doped, to obtain a highly doped layer 14, which may be the confinement layer 14 discussed above for supporting SPPs. For example, the doping may arrive at a concentration of charges in the range between $10^{19}$ m$^{-3}$ and $10^{21}$ cm$^{-3}$.

In the transition towards FIG. 3-3, a thin non-doped semiconductor layer 23 (e.g., in silicon dioxide) may be deposed over the highly doped layer (confinement layer) 14. The thin sublayer 23 (not shown in FIGS. 3-1 to 3-4) may be used to prevent the migration of dopants from the highly doped layer 14 (e.g., towards a subsequent non-doped semiconductor layer to be deposed subsequently). The thin non-doped semiconductor layer 23 may operate as a stop layer for performing the etching step that will form the pillars 12. The thin non-doped semiconductor layer 23 may help to confine SPP mode into the surface. The thin non-doped semiconductor layer 23 may be used for manufacturing the device 10 of FIG. 1. In alternative, when manufacturing the device 10a of FIG. 1a, no step for making the thin non-doped semiconductor layer 23 is provided.

A thick non-doped semiconductor layer 12' (e.g., in polysilicon) may be deposited over the thin non-doped semiconductor layer 22 and/or over the highly doped layer (confinement layer) 14. The thick non-doped semiconductor layer 12' may be the precursor of the pillars (rods) 12. The thickness of the thick non-doped semiconductor layer 12' may therefore be that of (or otherwise associated to) the vertical confinement length of the mode of the radiation to be vertically confined.

In the transition towards FIG. 3-4, material is selectively removed from the thick non-doped semiconductor layer 12', to obtain a pattern of pillars 12. The etching may be performed, e.g., in such a way to present mutual distances and/or diameters which permit lateral confinement according to bandgap engineering. Etching (e.g., dry etching) may be used. Photolithography techniques may be used.

Accordingly, a device such as the semiconductor device 10 or 10a may be obtained. The step of removing can be performed with higher reliability, as the pillars 12 have a reduced height as compared to the pillars that should be necessary for vertically containing the radiation without the use of the present techniques.

More in general, a manufacturing method 130 may comprise at least one of the following steps (shown in FIGS. 3-6):

doping a layer of a semiconductor (step 131), e.g., doping layer 14', to obtain a highly doped layer 14;

depositing a non-doped layer of semiconductor over the doped layer of semiconductor (step 132), e.g., depositing the layer 12' which is the precursor of the pillars 12;

selectively removing material from the non-doped layer of semiconductor 12' so as to obtain an array of pillars which form a photonic crystal for a specific wavelength (step 133), e.g., to arrive at the formation of the array of pillars 12.

Methods above may be performed using techniques such as silicon-on-insulator, SOI, techniques.

FIG. 4 shows a gas sensor 40, which may be a mid-IR gas sensor. The gas sensor 40 that may make use of the semiconductor device 10 or 10a. The gas sensor 40 may comprise a semiconductor device 10 or boa with the photonic crystal 11 and/or the waveguide 15. The gas sensor 40 may be used to measure, for example, the amount of a specific gas (e.g., within a mixture of gasses).

The gas sensor 40 may comprise a generator (radiation source) 41 upstream to the semiconductor device 10 or boa. The radiation source 41 may generate or emit (e.g., by filtering generated light) electromagnetic radiation (e.g., IR or visible light). The electromagnetic radiation may be generated at the specific wavelength or may be otherwise filtered.

In the semiconductor device 10 and in particular in the space 17 and mainly within the waveguide 15, a specific gas to be measured or a mixture of gasses containing the specific gas may be present. The specific gas may interact with the radiation. The specific wavelength of the radiation, propagating through the waveguide 17, may be the wavelength of maximum absorption of the specific gas.

The optical gas sensor 40 may comprise an optical detector 42 detecting electromagnetic radiation at the specific wavelength.

By detecting the electromagnetic radiation at the specific wavelength (e.g., by comparing the intensity of radiation at the specific wavelength as generated by the radiation source 41 and the intensity of radiation at the specific wavelength as detected by the detector 42), it is possible to determine (e.g., estimate) the amount of the specific gas. These operations may be performed by a controller 43, which may be a device which controls the radiation source 41 and which obtains the intensity information from the optical detector 42. The controller may be or comprise a digital equipment, such as a processor, which may be a digital signal processor, DSP.

There is the possibility of performing (e.g., by using at least part of the equipment such as that discussed above) a method 14o for measuring a quantity of specific gas, the specific gas being associated to a specific wavelength of maximum absorption. The method 140 may comprise at least one of:

confining, at least in a lateral direction and a vertical direction, the electromagnetic radiation at the specific wavelength of maximum absorption in an environment (e.g., space 17 or waveguide 15) including the specific gas (step 141, e.g., which may be implemented by method 130);

measuring the intensity of the electromagnetic radiation at the specific wavelength of maximum absorption to estimate the amount of the specific gas (step 142).

The measured intensity may be used to determine the quantity (amount) of the gas in the environment (e.g., 15). For example, the detected intensity may be compared to emitted intensity, so as to estimate the amount of the specific gas.

Reference has been made, above, to a sensor for sensing carbon dioxide. However, other gasses may be sensed, by opportunely choosing the structural and/or functional features of the semiconductor device 10 or 10a and/or the gas sensor 40. The following is a non-exhaustive list of wavelengths that can be used for determining the amount of each material (source: Wikipedia).

$O_2$: 0.763 μm $CO_2$: 4.26 μm, 2.7 μm, about 13 μm

CO: 4.67 μm, 1.55 μm, 2.33 μm, 4.6 μm, 4.8 μm, 5.9 μm $NO_2$-6.17-6.43 μm, 15.4-16.3 μm, 496 nm $N_2O$-7.73 μm, 1.52 μm, 4.3 μm, 4.4 μm, about 8 μm $HNO_3$-5.81 μm $NH_3$-2.25 μm, 3.03 μm, 5.7 μm $H_2S$-1.57 μm, 3.72 μm, 3.83 μm $SO_2$-7.35 μm, 19.25 μm HF-1.27 μm, 1.33 μm HCl-3.4 μm HBr-1.34 μm, 3.77 μm HI-4.39 μm hydrocarbons-3.3-3.5 μm, the C—H bond vibration $CH_4$-3.33 μm, 7.91±0.16 μm can also be used, 1.3 μm, 1.65 μm, 2.3 μm, 3.2-3.5 μm, about 7.7 μm $C_2H_2$-3.07 μm $C_3H_8$-1.68 μm, 3.3 μm $CH_3Cl$-3.29 μm $H_2O$-1.94 μm, 2.9 μm $O_3$-9.0 μm, also 254 nm (UV)

H$_2$O$_2$-7.79 μm alcohol mixtures-9.5±0.45 μm

HCHO-3.6 μm

HCOOH-8.98 μm

COS-4.87 μm

A method 150 for manufacturing the gas sensor 40 may be performed by at least one of the following steps:

performing the method 130 to obtain a semiconductor device having a photonic crystal as above; and applying an optical detector configured to detect the specific wavelength (step 151); and/or applying a radiation source (e.g., 41) configured to emit the radiation at the specific wavelength (step 152).

Methods of operating the gas sensor 40 and/or the semiconductor device 10 or 10a may be performed under the control of a processor (e.g., the controller 43). In particular, a non-transitory storage unit may contain instructions which, when executed by a processor, cause the processor to control a method above and/or the gas sensor 40 and/or the semiconductor device 10.

In examples, above, when referring to a particular wavelength, reference may be made to a narrowband containing the particular wavelength (e.g., with a tolerance of 1%, or 0.1%, or 0.01%, or even less, for example). The same may apply to the constructional features, such as heights and other measures.

In examples above, reference has always been made to array of pillars. This definition also comprises bi-dimensional arrays, i.e. matrixes, such as in FIG. 1.

The implementation in hardware or in software may be performed using a digital storage medium, for example cloud storage, a floppy disk, a DVD, a Blue-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some examples comprise a data carrier having electronically readable control signals, which are capable of cooperating with a programmable computer system, such that one of the methods described herein is performed.

Generally, examples may be implemented as a computer program product with a program code, the program code being operative for performing one of the methods when the computer program product runs on a computer. The program code may for example be stored on a machine-readable carrier.

Other examples comprise the computer program for performing one of the methods described herein, stored on a machine-readable carrier. In other words, an example is, therefore, a computer program having a program code for performing one of the methods described herein, when the computer program runs on a computer.

A further example is, therefore, a data carrier (or a digital storage medium, or a computer-readable medium) comprising, recorded thereon, the computer program for performing one of the methods described herein. A further example is, therefore, a data stream or a sequence of signals representing the computer program for performing one of the methods described herein. The data stream or the sequence of signals may for example be configured to be transferred via a data communication connection, for example via the Internet. A further example comprises a processing means, for example a computer, or a programmable logic device, configured to or adapted to perform one of the methods described herein.

A further example comprises a computer having installed thereon the computer program for performing one of the methods described herein.

In some examples, a programmable logic device (for example a field programmable gate array) may be used to perform some or all of the functionalities of the methods described herein. In some examples, a field programmable gate array may cooperate with a microprocessor in order to perform one of the methods described herein. Generally, the methods are preferably performed by any hardware apparatus.

The above described examples are merely illustrative for the principles above. It is understood that modifications and variations of the arrangements and the details described herein will be apparent to others skilled in the art. It is the intent, therefore, to be limited only by the scope of the impending patent claims and not by the specific details presented by way of description and explanation of the examples herein.

What is claimed is:

1. A semiconductor device, comprising:
    a pillar photonic crystal including a structure and a plurality of pillars extending from the structure in a height direction,
    wherein the plurality of pillars form at least one waveguide for electromagnetic radiation at a specific wavelength, the at least one waveguide extending in at least one planar direction,
    wherein the structure includes a confining layer in doped semiconductor material to support propagation of surface plasmon polaritons, and
    wherein the semiconductor material of the confinement layer has a concentration of charges between $10^{19}$ cm$^{-3}$ and $10^{21}$ cm$^{-3}$.

2. The semiconductor device of claim 1,
    wherein the height of the pillars in the height direction is associated to a length of a vertical mode distribution of electromagnetic radiation at the specific wavelength.

3. The semiconductor device of claim 1,
    wherein the confining layer has a thickness of between 50 nm and 150 in the height direction.

4. The semiconductor device of claim 1,
    wherein a relative permittivity of the doped semiconductor of the confinement layer is negative.

5. The semiconductor device of claim 1,
    wherein an imaginary part of a relative permittivity of the doped semiconductor is between −1 and 0.

6. The semiconductor device of claim 1,
    wherein the specific wavelength is 4.26 μm.

7. The semiconductor device of claim 1,
    wherein the specific wavelength is in a mid-infrared, IR, region.

8. An optical gas sensor for measuring the amount of a specific gas, comprising:
    the semiconductor device configured according to claim 1; and
    an optical detector to detect electromagnetic radiation at the specific wavelength, wherein the specific wavelength is a wavelength of maximum absorption of the specific gas; and
    the optical detector is configured to measure an intensity of electromagnetic radiation at the specific wavelength, so that the optical gas sensor determines the amount of the specific gas on the basis of an intensity of the electromagnetic radiation.

9. A method for spatially confining electromagnetic radiation at a specific wavelength, the method comprising:

confining electromagnetic radiation in a lateral direction through a pillar array extending in a height direction and forming a photonic crystal; and confining the electromagnetic radiation in a height direction by plasmonic effect, through a confinement layer extending in a planar direction perpendicular to the height direction, the confinement layer comprising a doped semiconductor material having a concentration of charges between $10^{19}$ cm$^{-3}$ and $10^{21}$ cm$^{-3}$.

10. A method for measuring a quantity of specific gas, the specific gas being associated to a specific wavelength of maximum absorption, the method comprising:

confining electromagnetic radiation at the specific wavelength of maximum absorption according to claim 9 in an environment including the specific gas; and measuring an intensity of the electromagnetic radiation at the specific wavelength of maximum absorption to estimate the amount of the specific gas.

11. A non-transitory storage unit containing instructions which, when executed by a processor in combination with the photonic crystal, cause the processor to control the method of claim 9.

12. A method for manufacturing a semiconductor device, comprising:

doping a layer of a semiconductor;

depositing a non-doped layer of semiconductor over the doped layer of semiconductor; and selectively removing material from the non-doped layer of semiconductor so as to obtain an array of pillars forming a photonic crystal for a specific wavelength, wherein depositing the non-doped layer of semiconductor includes depositing the non-doped layer to have a thickness which is a length or a multiple of the length of a vertical mode distribution of electromagnetic radiation at the specific wavelength.

13. A method for manufacturing an optical gas sensor for measuring the amount of a specific gas, the method comprising:

performing the method of claim 12; and applying an optical detector configured to detect the specific wavelength.

* * * * *